Nov. 19, 1935. A. F. J. BAUR Plant Pat. 148
SCARLET CARNATION
Filed June 3, 1935
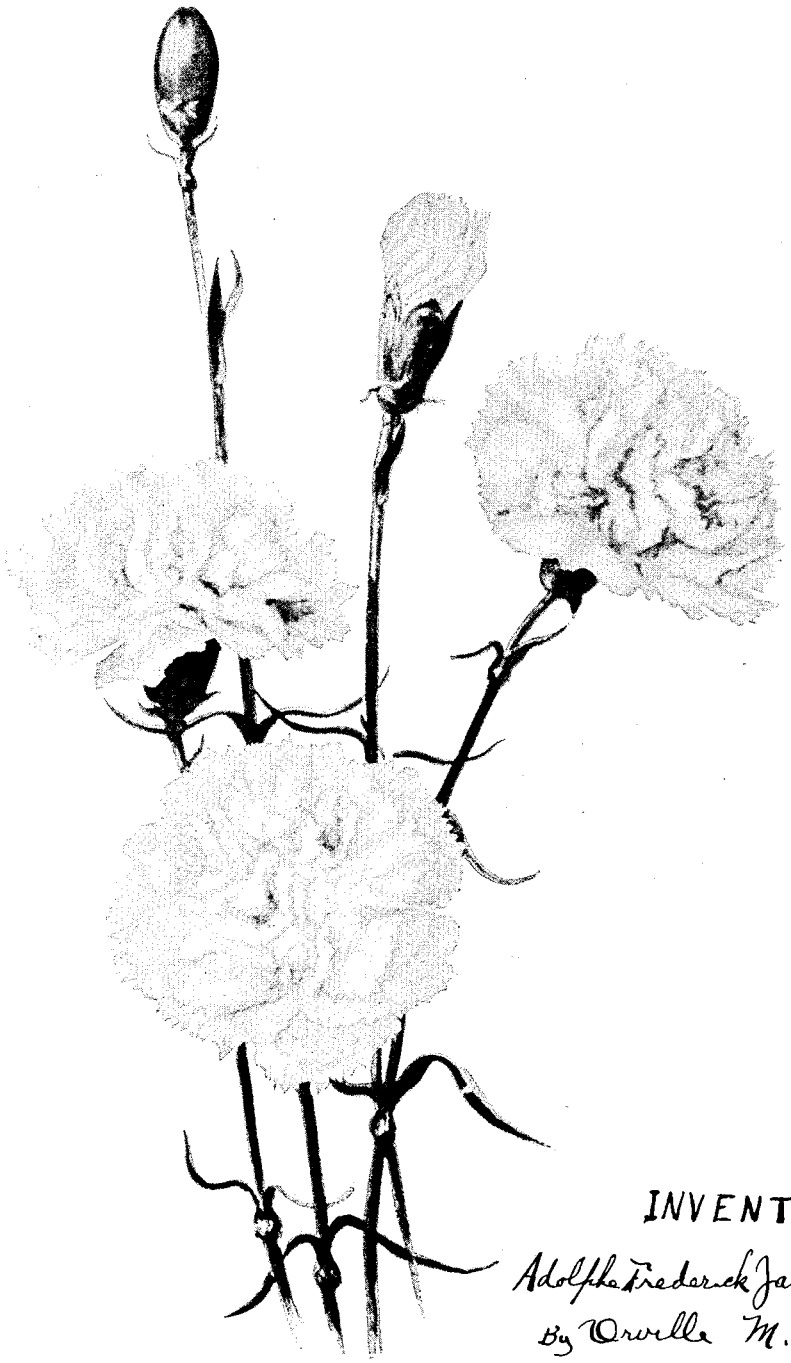
INVENTOR
Adolphe Frederick Jacob Baur
By Orville M. Kile
Plant Patent Agent Patented Nov. 19, 1935

Plant Pat. 148

UNITED STATES PATENT OFFICE

148

SCARLET CARNATION

Adolphe Frederick Jacob Baur, Indianapolis, Ind., assignor to Baur-Steinkamp and Company, Incorporated, Indianapolis, Ind.

Application June 3, 1935, Serial No. 24,763

1 Claim. (Cl. 47—60)

My new variety, which produced its first bloom in September, 1931, came from a line of seedlings starting with the varieties Radiolite and Spectrum, two leading scarlet carnation varieties in their time. Of these two varieties, each had merits developed to a very high degree but also faults that were very serious. Singularly, however, each variety was strong in the features in which the other was deficient. So I undertook the task, in 1927, of combining the good qualities of these two varieties in one variety and of eliminating the faults. By crossing and recrossing over a period of four years I found among the seedlings a plant which seemed to fill these requirements. Subsequent years of testing have substantiated my first estimate of this seedling variety and I have now increased the stock sufficiently to have fully established its character.

My new variety has the rich scarlet color of the well known variety Radiolite. It also has the strong stem and non-splitting calyx of that variety. The flower is larger and has more petals and is, therefore, a better formed flower. It has inherited from Spectrum its freedom in growth and flowering and also its fine keeping quality. Thus I have eliminated the shy blooming habit of Radiolite and the weak stem and calyx splitting of Spectrum.

The accompanying illustrations show in full color but somewhat reduced size, a closed bud, an opening bud and several views of the fully opened flower, also stems and foliage.

The following is a detailed description of my new variety of carnation:

*The plant* is vigorous and upright in growth, usually attaining 3 to 4 feet in height, and well supplied with foliage. The stems are notably strong and sturdy. This variety flowers freely.

*Flowers.*—Rich scarlet in color, approximately "scarlet-red" according to Ridgway's Color Standards and Nomenclature (Plate I). The color is rather evenly distributed over the visible parts of the flower as viewed from above. On the underneath side of the petals the color is slightly lighter. Only a very slight amount of white shows at the top of the calyx although each petal is white or greenish on that portion inside the calyx. The pinkish style divides into three branches and the tips are straight rather than curling and do not protrude into visibility among the petals, as occurs in the somewhat similar variety Satellite which has a two-branching style.

Under ordinary good culture the flowers attain a diameter of 3½ to 4 inches. This extraordinary size is due in part to the length of the petals and in part to the large number of large petals. A large ovary also adds to the size of the flower. In the month of May under greenhouse conditions, typical flowers have 44 to 48 large petals and practically no small or rudimentary petals.

All, or nearly all, of the individual petals of the variety are prominently notched or serrated along the entire upper edge. Many of the petals have one very deep notch or cut in addition to the serrations. Many of the petals are partially folded and longitudinally curled, which gives a somewhat crinkled appearance.

This variety produces a dozen to fifteen well developed stamens 1 to 1½ inches long. The anthers are small, brownish bodies but some of the stamens are topped with a minute leaf-like growth apparently not pollen-bearing.

The general form of the flower is ranked as excellent, having a well-rounded full center and being pleasingly regular.

The flower is only moderately fragrant.

This variety has excellent keeping qualities.

*Calyx.*—Of moderate length but broad and strong. The non-splitting character of the calyx, so important in a large, heavy flower, is a notable feature of this new variety. Four prominent bracts at the base of the calyx add to both the strength and to the beauty.

*Buds.*—Elongated rather than ball shaped.

*Stems and foliage.*—Stems are long, straight, and strong, usually growing 30 to 36 inches in length. The strong, sturdy structure of the stems is an important feature of this variety and a necessity in a variety having such large, heavy flowers. The leaves are medium broad and of medium length, curling but slightly.

The color of stems and leaves is dark bluish green, overlaid with a light to moderate gray bloom. The nodes are considerably enlarged and prominent.

The more important features which distinguish my new variety from the known variety which it somewhat resembles, namely Satellite, are:

First, its larger and fuller flowers.

Second, its brighter and richer color of blossom.

Third, its stronger stems, more profuse foliage and more vigorous growth.

Fourth, its three-branching non-curled style as compared with Satellite's two-branched, curling style.

Fifth, its numerous large stamens with anthers, as contrasted with almost no stamens and apparently no anthers in Satellite.

Having thus disclosed my invention, I claim:

The variety of carnation herein shown and described, characterized particularly by its very large, full flowers of rich scarlet color, its vigorous growth and profuse flowering habits, its strong non-splitting calyx and fine keeping qualities.

ADOLPHE FREDERICK JACOB BAUR.